US009216077B2

(12) United States Patent
Davis et al.

(10) Patent No.: US 9,216,077 B2
(45) Date of Patent: Dec. 22, 2015

(54) MEDICAL CONSTRUCTS OF TWISTED LENGTHS OF COLLAGEN FIBERS AND METHODS OF MAKING SAME

(75) Inventors: Tian Davis, Ruskin, FL (US); Thomas J. Koob, Tampa, FL (US)

(73) Assignee: MiMedx Group, Inc., Marietta, GA (US)

( * ) Notice: Subject to any disclaimer, the term of this patent is extended or adjusted under 35 U.S.C. 154(b) by 1031 days.

(21) Appl. No.: 12/465,433

(22) Filed: May 13, 2009

(65) Prior Publication Data
US 2009/0287308 A1 Nov. 19, 2009

Related U.S. Application Data

(60) Provisional application No. 61/053,901, filed on May 16, 2008.

(51) Int. Cl.
*A61F 2/08* (2006.01)
*A61L 27/24* (2006.01)
*D02G 3/10* (2006.01)
*D02G 3/44* (2006.01)

(52) U.S. Cl.
CPC . *A61F 2/08* (2013.01); *A61L 27/24* (2013.01); *D02G 3/10* (2013.01); *D02G 3/448* (2013.01); *A61F 2210/0004* (2013.01); *A61F 2210/0057* (2013.01); *A61F 2250/0017* (2013.01); *A61F 2250/0028* (2013.01); *A61F 2250/0036* (2013.01); *A61F 2250/0039* (2013.01); *A61L 2430/10* (2013.01)

(58) Field of Classification Search
CPC .................................................. A61L 27/3662
See application file for complete search history.

(56) References Cited

U.S. PATENT DOCUMENTS

| 3,316,699 A | 5/1967 | Mattingly |
| 4,590,928 A | 5/1986 | Hunt et al. |
| 4,792,336 A | 12/1988 | Hlavacek et al. |
| 4,841,962 A | 6/1989 | Berg et al. |
| 4,883,486 A | 11/1989 | Kapadia et al. |
| 4,979,956 A | 12/1990 | Silvestrini |
| 5,078,744 A | 1/1992 | Chvapil |
| 5,106,949 A | 4/1992 | Kemp et al. |

(Continued)

FOREIGN PATENT DOCUMENTS

| CA | 2285161 | 4/2001 |
| EP | 1493404 | 1/2005 |

(Continued)

OTHER PUBLICATIONS

Becker et al., Early active motion following a beveled technique of flexor tendon repair: Report on fifty cases, Journal of Hand Surgery, 1979, vol. 4 No. 5, pp. 454-460.

(Continued)

*Primary Examiner* — Yashita Sharma
*Assistant Examiner* — Rebecca Preston
(74) *Attorney, Agent, or Firm* — Myers Bigel Sibley & Sajovec, P.A.

(57) ABSTRACT

Medical constructs that have a plurality of NDGA-treated collagen fibers twisted together to provide strands that are twisted together into implantable cords. The cords are suitable to treat orthopaedic and other conditions and can be degradeable over time. Related and methods of twisting the collagen fibers as groups or bundles of fibers to form the medical constructs are described.

2 Claims, 8 Drawing Sheets

(56) References Cited

U.S. PATENT DOCUMENTS

| | | | |
|---|---|---|---|
| 5,256,418 A | | 10/1993 | Kemp et al. |
| 5,263,984 A | | 11/1993 | Li et al. |
| 5,378,469 A | * | 1/1995 | Kemp et al. .................. 424/423 |
| 5,569,302 A | * | 10/1996 | Proto et al. ................... 606/228 |
| 5,656,605 A | | 8/1997 | Hansson et al. |
| 5,713,374 A | | 2/1998 | Pachence et al. |
| 5,718,012 A | | 2/1998 | Cavallaro |
| 5,718,717 A | | 2/1998 | Bonutti |
| 6,090,117 A | | 7/2000 | Shimizu |
| 6,224,630 B1 | | 5/2001 | Bao et al. |
| 6,277,397 B1 | | 8/2001 | Shimizu |
| 6,280,474 B1 | | 8/2001 | Cassidy et al. |
| 6,292,697 B1 | | 9/2001 | Roberts |
| 6,335,007 B1 | | 1/2002 | Shimizu et al. |
| 6,531,147 B2 | | 3/2003 | Sawhney et al. |
| 6,565,960 B2 | | 5/2003 | Koob et al. |
| 6,589,257 B1 | | 7/2003 | Shimizu |
| 6,592,623 B1 | | 7/2003 | Bowlin et al. |
| 6,645,247 B2 | | 11/2003 | Ferree |
| 6,692,528 B2 | | 2/2004 | Ward et al. |
| 6,713,537 B1 | | 3/2004 | Ueda et al. |
| 6,730,124 B2 | | 5/2004 | Steiner |
| 6,752,831 B2 | | 6/2004 | Sybert et al. |
| 6,821,530 B2 | | 11/2004 | Koob et al. |
| 6,866,681 B2 | * | 3/2005 | Laboureau et al. .......... 623/13.2 |
| 6,936,072 B2 | | 8/2005 | Lambrecht et al. |
| 6,955,683 B2 | | 10/2005 | Bonutti |
| 7,084,082 B1 | | 8/2006 | Shimizu |
| 7,090,690 B2 | | 8/2006 | Foerster et al. |
| 7,115,146 B2 | | 10/2006 | Boyer et al. |
| 7,135,040 B2 | | 11/2006 | Wang et al. |
| 7,309,359 B2 | | 12/2007 | Trieu et al. |
| 7,354,627 B2 | | 4/2008 | Pedrozo et al. |
| 7,650,742 B2 | * | 1/2010 | Ushijima ........................ 57/238 |
| 2001/0018619 A1 | | 8/2001 | Enzerink et al. |
| 2001/0044659 A1 | | 11/2001 | Laboureau et al. |
| 2002/0037940 A1 | | 3/2002 | Koob et al. |
| 2002/0123805 A1 | | 9/2002 | Murray et al. |
| 2003/0100108 A1 | | 5/2003 | Altman et al. |
| 2003/0230316 A1 | | 12/2003 | Glucksman et al. |
| 2004/0110439 A1 | | 6/2004 | Chaikof et al. |
| 2004/0131562 A1 | | 7/2004 | Gower et al. |
| 2004/0193241 A1 | | 9/2004 | Stinson |
| 2004/0224406 A1 | | 11/2004 | Altman et al. |
| 2004/0267362 A1 | | 12/2004 | Hwang et al. |
| 2005/0033362 A1 | | 2/2005 | Grafton |
| 2006/0095134 A1 | | 5/2006 | Trieu et al. |
| 2006/0257377 A1 | | 11/2006 | Atala et al. |
| 2006/0263417 A1 | | 11/2006 | Lelkes et al. |
| 2007/0118217 A1 | | 5/2007 | Brulez et al. |
| 2007/0248643 A1 | | 10/2007 | Devore et al. |
| 2008/0020012 A1 | | 1/2008 | Ju et al. |
| 2008/0038352 A1 | | 2/2008 | Simpson et al. |
| 2008/0124371 A1 | | 5/2008 | Turos et al. |
| 2008/0161917 A1 | | 7/2008 | Koob et al. |
| 2008/0188933 A1 | | 8/2008 | Koob et al. |
| 2008/0200992 A1 | | 8/2008 | Koob et al. |
| 2008/0215150 A1 | | 9/2008 | Koob et al. |
| 2008/0300683 A1 | * | 12/2008 | Altman et al. ............. 623/13.11 |
| 2009/0216233 A1 | | 8/2009 | Wiedrich et al. |

FOREIGN PATENT DOCUMENTS

| | | |
|---|---|---|
| WO | WO 93/06790 | 4/1993 |
| WO | WO 96-14095 | 5/1996 |
| WO | WO 01-72241 | 10/2001 |
| WO | WO 2008-041183 | 4/2008 |

OTHER PUBLICATIONS

Brunelli et al., Slip-knot flexor tendon suture in zone II allowing immediate mobilisation, The Hand, 1983, vol. 15, pp. 352-358.

Greis et al, The influence of tendon length and fit on the strength of the tendon-bone tunnel complex, Am. J. Sports Med., 2001, 29:493-497.

Koob et al., Material properties of NDGA-collagen composite fibers: development of biologically based tendon constructs, Biomaterials, 2002, 23:202-212.

Koob et al., Mechanical and thermal properties of novel polymerized NDGA-gelatin hydrogels, Biomaterials, 2003, 24:1285-1292.

Messina, The double armed suture: Tendon repair with immediate mobilization of the fingers, Journal of Hand Surgery, 1992, 17A:137-142.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British Volume, 1989), 14B:396-399.

Silva et al., The insertion site of the canine flexor digitorum profundus tendon heals slowly following injury and suture repair, J. Orthop. Res., 2002, 20:447-453.

Trotter et al., Molecular structure and functional morphology of echinoderm collagen fibrils, Cell Tiss. Res., 1994, 275: 451-458.

International Search Report and Written Opinion for corresponding PCT application No. PCT/US2009/002971, Date of mailing Jan. 4, 2010.

International Preliminary Report on Patentability for corresponding PCT application No. PCT/US2009/002971, Date of mailing Nov. 25, 2010.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Koob et al., Biocompatibility of NDGA-polymerized collagen fibers. I. Evaluation of cytotoxicity with tendon fibroblasts in vitro, © 2001 John Wiley & Sons, Inc.

Koob et al., Biocompatibility of NDGA-polymerized collagen fibers. II. Attachment, proliferation, and migration of tendon fibroblasts in vitro, © 2001 John Wiley & Sons, Inc.

Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

Nottage et al., Arthoscopic Knot Tying Techniques, Arthroscopy: The Journal of Arthroscopic & Related Surgery 15(1999): 515-521.

Integra™ NeuraGen™ Nerve Guide, Product Broacher, 4 pages 2005.

Integra™ NeuraGen™ Nerve Guide, Product Webpage, http://www.integra-Is.com/products/?product=88, Date Unknown but believed to be prior to the filing date of the present application, 2 pages.

Integra™ NeuraWrap™ Nerve Protector, Product Webpage, http://www.integra-Is.com/products/?product=198, Date Unknown but believed to be prior to the filing date of the present application, 2 pages.

Product advertisement,Conair QB3ECS Quick Braid Styling Kit, © 2007(1 page).

Koob, Thomas J., Biomimetic approaches to Tendon Repair, Comparative Biochemistry and Physiology Part A 133 (2002)1171-1192.

* cited by examiner

MEDICAL CONSTRUCTS OF TWISTED LENGTHS OF COLLAGEN FIBERS AND METHODS OF MAKING SAME

RELATED APPLICATIONS

This application claims the benefit of priority of U.S. Provisional Application Ser. No. 61/053,901 filed May 16, 2008, the contents of which are hereby incorporated by reference as if recited in full herein.

FIELD OF THE INVENTION

The invention relates to medical constructs.

BACKGROUND OF THE INVENTION

It is believed that the linear organization of natural collagen fibers in tendons results in optimal stiffness and strength at low strains under tensile loads. However, this organization makes repairing tissue such as ruptured or lacerated tendons difficult. Current suturing techniques to join split ends of tendons, while providing sufficient mechanical strength to prevent undue gapping, are often inadequate to carry normal loads and may not ever allow the tendon to regain its original mechanical properties or mobility. Immobilization protocols used to restore tendon congruity may result in scar formation at the repair site and peripheral adhesions that can limit excursions. One or more similar issues may be associated with conventional ligament repair techniques.

SUMMARY OF EMBODIMENTS OF THE INVENTION

Embodiments of the present invention are directed to medical constructs that provide new and alternative medical treatment or repair devices.

Embodiments of the present invention provide implantable cables, (e.g., cords, yarns, sutures or ropes) having a plurality of collagen fibers twisted together.

In some embodiments, the fibers can consist essentially of collagen fibers, e.g., NDGA-treated collagen fibers ad the construct can have a multi-directional twist configuration (e.g., some twists in a CW direction and others in a CCW direction over at least a major portion of a length of the construct).

Some embodiments are directed to medical constructs that include a biocompatible cable having a plurality of NDGA treated elongate collagen fibers twisted together a number of turns per fiber meter along a length thereof. The cable has a multi-directional twist configuration with some twists associated with discrete fibers or strands being in a first rotative direction (CW or CCW) and other twists associated with strands twisted together associated with an opposing rotative (CW or CCW) direction, the different twist directions extending over at least a major portion of a length of the cable.

In particular embodiments, the plurality of fibers are a plurality of separate strands of at least two fibers, the separate strands each having a respective first number of twists of between about 10-1000 twists per fiber meter in the first rotative (CW or CCW) direction. The construct is configured with the plurality of twisted strands being twisted together with between about 10-1000 twists per fiber meter in the opposing rotative (CCW or CW) direction to define an interlocking multi-directional twisted construct configuration.

In some embodiments, the cable has between about 90-270 fibers, wherein the first number of twists per strand is substantially the same for each strand. The twisted strands are twisted together with between about 50% to about 300% of the number of twists per fiber meter as the twists in the separate fiber strands.

In some particular embodiments, the cable is a 30 NDGA treated collagen fiber cable, having a 10×3 configuration whereby there are 10 individually twisted fibers per strand and 3 of the 10 strands are twisted together.

In some embodiments, the cable is a 108 NDGA treated collagen fiber cable, having a 4×3×3×3 configuration whereby there are: (a) 4 individually twisted fibers/strand; (b) 3 strands of the 4 twisted fibers of (a) twisted together; (c) 3 of the twisted construct of (b) twisted together; and (c) 3 of the twisted constructs of (c) twisted together.

In other embodiments, the cable is a 180 NDGA treated collagen fiber cable having a 20×3×3 configuration whereby there are: (a) 20 fibers individually twisted/strand×3 strands twisted together; then (b) 3 of the construct of (a) (20×3 or 60 fibers) twisted together (3×60), and wherein the number of (b) twists is between about 200-300 twists per meter.

In particular embodiments, the cable has NDGA treated elongate collagen fibers with a configuration of A×B×C, whereby there are: (i) a number "A" of discrete fibers or separate groups of fibers each having a number of twists per fiber meter; (ii) a number "B" of groups of the twisted A fibers or groups of fibers twisted together; and (iii) a number "C" of the B groups twisted together. The twisted fibers or groups of fibers of (i) have a number of twists per fiber meter between about 100-300 on average, and the fiber groups of "B" and "C" are twisted together with between about 100-300 per fiber meter on average.

The number of discrete collagen fibers or separate groups of collagen fibers in "A" can be a number between about 2-100, and the number of twisted fiber groups of "B" and "C" can be between about 2-12.

Other embodiments are directed to methods of making a medical construct. The methods include: (a) providing a plurality of discrete elongate untwisted NDGA treated collagen fibers or untwisted NDGA treated collagen fiber bundles; and (b) first twisting each the fibers or fiber bundles in one of a counterclockwise or counterclockwise direction; then (c) secondly twisting the first twisted fibers or fiber bundles together in the opposing direction to form a twisted medical construct.

The second twisting step can be carried out so that the twists per fiber meter created by the second twisting step is between about 50-300% of the twists per fiber meter created by the first twisting step, and wherein the first and second twisting steps are carried out while the fibers are held in tension.

In some embodiments, the method may also include, after the second twisting step, twisting a plurality of the second twisted fiber groups together to form the twisted medical construct. The first twisting step can have a twist density of between about 90-200 twists per fiber meter, and the second and third twisting steps can have a twist density of between about 200-300 twists per fiber meter.

In some embodiments, the medical construct has between about 90-300 discrete elongate NDGA treated collagen fibers.

In some embodiments, the construct may define a construct for spinal stabilization, constructs for use in repair of the AC, ACL, and/or UCL, and cerclage constructs such as for use in treatment or repair of oblique bone fractures or soft tissue. Some embodiments provide constructs for use in stabilizing bone in Hallus valgus/Hallax valgus correction procedures.

In some embodiments, the NDGA-polymerized collagen fibers are bundles of fibers that are arranged to be substantially parallel to each other in a respective bundle. The cables can comprise any suitable number of strands (fibers), typically between about 2-4000, and more typically between about 30-360. The strands can comprise between about two (2) fibers per bundle to about twelve hundred (1200) fibers per bundle. Each bundle can have the same or a different number of fibers. Typically, at least three bundles of the fibers are twisted together to form the cable.

Yet other embodiments are directed to a medical kit for a tendon or ligament repair, augmentation or replacement. The kit includes: (a) a twisted (NDGA) collagen fiber cable and (b) a sterile package sealably enclosing the twisted fiber construct therein.

Further features, advantages and details of the present invention will be appreciated by those of ordinary skill in the art from a reading of the figures and the detailed description of the embodiments that follow, such description being merely illustrative of the present invention.

DETAILED DESCRIPTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. In the figures, broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" and "construct" are used interchangeably herein to designate an implantable medical product configured to repair or replace (at least a portion of) tissue, typically soft tissue, such as, for example, muscle, a natural tendon, ligament (e.g., ACL), AC joint, or other skin or tissue of a mammalian subject (for veterinary or medical (human) applications). The term "implantable" means the device can be inserted, embedded, grafted or otherwise attached or placed on or in a patient.

Unless stated otherwise herein, all measurements of size refer to measurements taken on dry cables or fibers. The term "collagen fibers" refers to natural and synthetic collagen-derived fiber materials. Collagen "microfibrils," "fibrils," and "natural fibers" refer to naturally-occurring structures found in a tendon. Microfibrils are about 3.5 to 50 μm in diameter. Fibrils are about 50 nm to 50 μm in diameter. Natural fibers are above 50 μm in diameter. A "synthetic fiber" refers to any fiber-like material that has been formed and/or chemically or physically created or altered from its naturally-occurring state. For example, an extruded collagen fiber of fibrils formed from a digested tendon is a synthetic fiber but a tendon fiber newly harvested from a mammal is a natural fiber. Synthetic collagen fibers can include non-collagenous components, typically non-structural components, such as particulates, hydroxyapatite and other mineral phases, or drugs that facilitate tissue growth. See, U.S. Pat. No. 6,821,530, hereby incorporated by reference herein. For example, the compositions can contain carbon nano-tubes, zinc nano-wires, nano-crystalline diamond, or other nano-scale particulates, and larger crystalline and non-crystalline particulates such as calcium phosphate, calcium sulfate, and apatite minerals. For example, the fibers and/or constructs formed of the fibers can include compositions that contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. In some embodiments, the fibers and/or constructs can contain cells, engineered cells, stem cells, and the like, as well as combinations of the above.

Excluding fixation hardware and coatings or devices on end portions of the construct bodies that inhibit unraveling, the construct bodies 30 can consist essentially of collagen fibers, which may, in some embodiments, be NDGA-treated collagen fibers. The collagen fiber construct may also include supplemental biocompatible material that does not affect the structural mechanical behavior of the twisted collagen fibers. That is, the twisted constructs of elongate NDGA treated collagen fibers have sufficient structural mechanical properties to provide the desired mechanical strength and flexibility for a particular use without (devoid of) additional reinforcing material such as silk threads.

Where the construct is a suture, it can be configured as an absorbable, partially absorbable or non-absorbable biocompatible material, In some particular embodiments, the suture constructs may include supplemental materials. Examples of "supplemental" suture materials include elastomeric materials, such as, for example, polymers, copolymers and/or derivatives thereof, including Vicryl(V Polymer, as well as other materials including, for example, NITINOL, and combinations thereof. The sutures may be used to with a suture anchor (bone or tissue anchor).

The term "atraumatic" with respect to suture needles with thread refers to an atraumatic or eyeless needle attached to a specific length of suture material (thread or filament). The suture and needle are preformed and purchased as a unit, as the suture needle manufacturer swages or binds the suture thread to the eyeless atraumatic needle at the factory. In a conventional traumatic needle with suture, the thread comes out of the needle's hole or eye on both sides. When passing through the tissues, this type of suture may rip tissue, at least to a certain extent. In contrast to the conventional "trauma"-type needle with suture, the atraumatic needle with suture does not cause trauma (hence the name "atraumatic"). Because of these advantages, atraumatic needles with sutures are today very widely used.

As with conventional sutures, the sutures of atraumatic needles can be absorbable or non-absorbable. As is well known, there are several shapes of atraumatic needles, including straight, half curved, one-third curved and others. The body of the needle is available also in different makes, like circular, with edge on the outer side, with edge on the inner side, and others.

The term "flexible" means that the so-called member can be flexed or bent. In some embodiments, the twisted construct is resiliently flexible and has high tensile strength. The term "biodegradable" means that the material dissolves, is absorbed, resorbed or otherwise is decomposed by natural body processes over time.

The term "twisted" and derivatives thereof mean to entwine two or more fibers or two or more strands of fibers into a single body having a number of twists per defined length, such as between about 10-1000 twists per fiber meter.

The twisted configuration can be formed by individually turning separate fibers or groups of fibers (e.g., single fiber or multi-fiber strands) in a first rotative direction (e.g., one of a CW or CCW direction) to introduce a series of turns/twists extending along a lengthwise direction, including manually or automatically twisting the fibers and/or fiber bundles. A plurality of these separate twisted fibers/strands can then be twisted together in an opposing rotative direction to form an interlocking multi-twist directional construct.

The term "cable" is used interchangeably with the word "cord" and derivatives thereof and means twisted lengths of elongate fibers and/or fiber bundles. The cables can have any suitable cross-sectional area or diameter. The cable can be configured to retain its mechanical structure and act as a bioprosthesis and/or can act as a suture to hold a bioprosthesis in location for at least an initial post-implantation period of at least about one week, typically at least two weeks, and is typically substantially biodegradeable (e.g., absorbable) over time.

In some embodiments, the cables can have a cross-sectional area or diameter on average (measured on dry cable) that is between about 0.5 mm to about 1 cm, typically between about 1 mm to about 5 mm. In some particular embodiments, the cables may be smaller, such as between 0.0 mm to about 0.7 mm. The term "suture" refers to twisted constructs of collagen fibers of relatively smaller dimensioned cables or cordages typically in the range of between about 0.01 mm to about 0.7 mm, although smaller sizes may also be used, depending on the target repair. The term "rope" can be used to refer to cables of twisted fibers of larger dimensioned cables or cords with a diameter or average cross-sectional area (dry) that is about 5 mm to about 1 cm. The cables can be described as medical constructs and are typically sufficiently pliable to allow knots to be formed therewith. Thus, as used herein, the use of certain descriptive terms with respect to the constructs or cables (e.g., sutures versus ropes) of embodiments of the invention correlate to size rather than actual use. So, for example, a twisted suture can be used as a small cable for repairs, not just used in a conventional suture manner. Hence, as contemplated by embodiments of the invention, a twisted suture can be used alone or as a primary structure to repair a target site or may be used to attach a bioprosthesis to a target anatomical structure to help hold the bioprosthesis in location in the body.

It may also be appropriate to identify the construct in terms of denier, e.g., for round monofilaments, the denier may be calculated by the formula Denier=$d^2K$, where d is the diameter of a fiber expressed in mils (1 mil=1/1000 inch) (on average, measured dry). K is a constant for a particular material (e.g., collagen fibers). PEEK has a K value of 5.9, polyester 6.3, and polypropylene has a K value of 4.1 See, e.g., Sabit Adanur, *Paper Machine Clothing*, p. 68, (copyright 1997, Asten, Inc.); ISBN No. 1-56676-544-7. In some embodiments, NDGA treated collagen can have a K value of about 5.1. In particular embodiments, the twisted construct of collagen fibers 30 may have a denier that is between about 20 to about 80, such as, for example, about 40 denier (e.g., the latter associated with a d=2.8 mils and a K value of about 5.1).

Figure 1A:
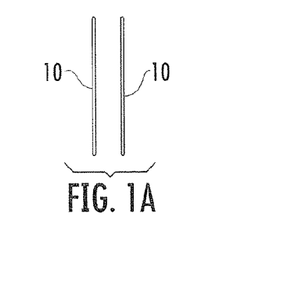
FIG. 1A is a schematic illustration of strands of fibers used to form a twisted construct according to embodiments of the present invention.
Figure 1B:
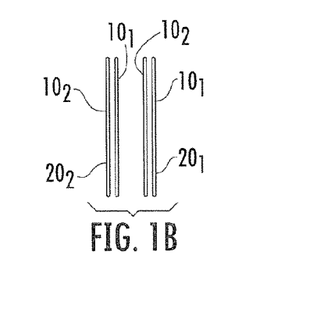
FIG. 1B is a schematic illustration of a two fiber, two strand/bundle used to form a twisted medical construct according to embodiments of the invention.
Figure 2A:
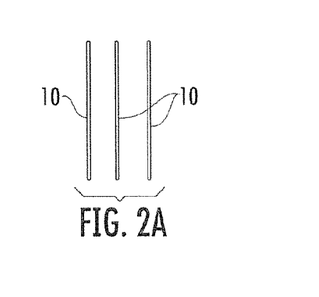
FIG. 2A is a schematic illustration of a three strand grouping of fibers used to make a twisted medical construct according to embodiments of the present invention.
Figure 2B:
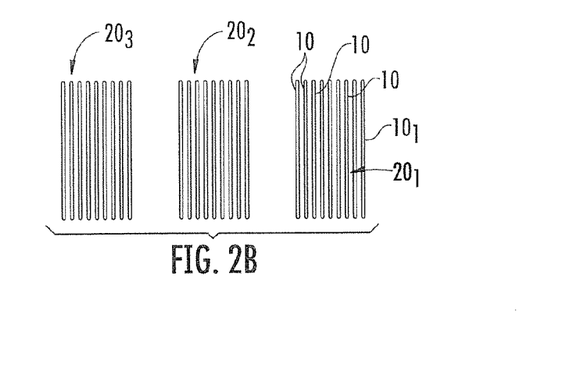
FIG. 2B is a schematic illustration of a three strand grouping of multiple fibers in each strand/bundle used to make a twisted construct according to embodiments of the present invention.
Figure 2C:
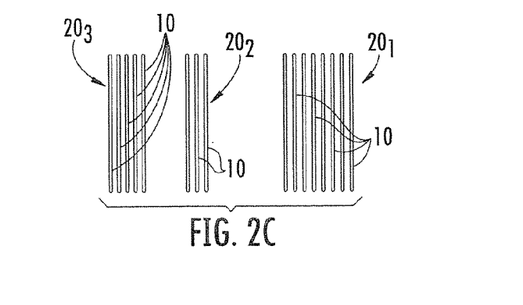
FIG. 2C is a schematic illustration of a three strand grouping of multiple fibers where at least one of the strands has a different numbers of fibers than another.
Figure 2D:
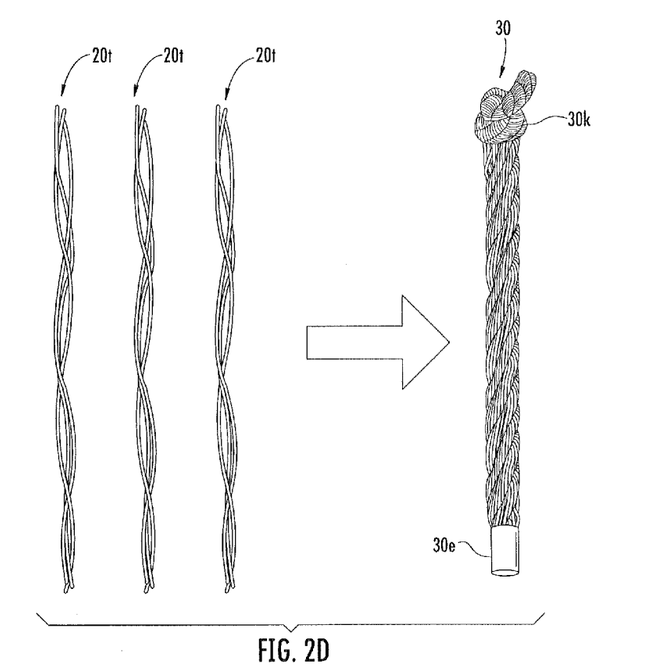
FIG. 2D is a schematic illustration of three twisted strands twisted together to form a single twisted construct according to embodiments of the present invention.

FIG. 1A is a schematic illustration of a plurality of elongate substantially parallel fibers 10 (shown as two) fibers $10_1$, $10_2$ that can be used to form a twisted cable, rope or suture 30 (see, e.g., FIG. 2D). FIG. 1B illustrates that the fibers 10 can each be formed into a plurality of discrete bundles (or strands) 20, shown as two fibers 10 in two bundles (e.g., strands) $20_1$, $20_2$.

FIGS. 2A-2C illustrate that the fibers 10 can be formed into three discrete groups (which can be discrete or separate fiber or strands or bundles of the fibers). FIG. 2A illustrates the groups can comprise at least one fiber 10 each. FIG. 2B illustrates that the three groups (strands or bundles) $20_1$, $20_2$, $20_3$ can each include a plurality of fibers from $10_1$-$10_n$, where n=10 in the embodiment shown. FIG. 2C illustrates that not every group (strand or bundle) $20_1$, $20_2$, $20_3$ need have the same number of fibers (shown here as two of the bundles $20_1$, $20_3$ having six fibers and one having three fibers). The fibers 10 in each bundle 20 or all fibers in all bundles 20 can have the same size (e.g., average cross-sectional area or diameter) or each or selected ones may vary to be larger or smaller than others in a bundle or between bundles. One or more of the fibers 10 in a bundle 20 may be discontinuous over a bundle/strand length or may terminate before the end of the construct 30. The fibers have a cross-sectional size, on average, of between about 0.001 inches to about 0.1 inches.

The number of fibers 10 and the number of strands/bundles 20 can vary depending on the mechanical properties and shape desired and the twisting equipment used to form the construct. The twisted construct has a scalable configuration (e.g., numbers of fibers and/or bundles) that can be varied for performance characteristics or target repairs. Twisting of the strands or bundles can be done once (e.g. 10 (untwisted) fibers in a strand twisted with two other bundles of the same configuration forms a 30 fiber cable), or can be twisted in a variety of other configurations.

The constructs 30 can comprise any suitable number of fibers, typically between about 2-4000, and more typically between about 30-360. The strands can comprise between about two (2) fibers per strand to about sixty (60) fibers per bundle. In some embodiments, the implantable construct 30 can have between about 2-60 fibers 10 per strand or bundle 20 and between about 2-30 strands. Each bundle/strand can have the same or a different number of fibers than another bundle/strand. In some embodiments, at least three bundles/strands of multiple fibers are twisted together to form the construct 30.

In some embodiments, the construct or cable 30 can have NDGA treated elongate collagen fibers with a configuration of "A"×"B"×"C", whereby there are: (i) a number "A" of discrete fibers or separate groups of fibers each having a number of twists per fiber meter; (ii) a number "B" of groups of the A twisted fibers or groups of fibers twisted together; and (iii) a number "C" of the B strands twisted together. The number of fibers or strands of fibers in "A" can be a number between about 2-100. The number of twisted fibers or twisted fiber bundles of "B" and "C" can be a number between about 2-12.

The number of twists used for A, B and C can be different or substantially the same. The number of twists for "B" and "C" can be between about 50-300% of the number of twists of "A". For example, the separate fibers or groups of fibers of (A) can have about 100 twists per fiber meter, on average, and those twisted fibers or groups of fibers of (B) and/or (C) can be twisted together with about 200-300 twists per meter, on average.

In particular embodiments, the construct 30 is a 90 collagen fiber construct with about 300 twists per meter, on average. In other embodiments the construct 30 is a 180 fiber construct with between about 234-269 twists per meter, on average.

FIG. 2D illustrates that the three bundles or strands of fibers shown in FIGS. 2B-2C can each be twisted (individually) first, then those three twisted strands 20*t* can be twisted together (typically in an opposing clockwise or counterclockwise direction) to form the twisted construct 30, e.g., cable 30*c*, suture 30*s* or rope 30*r*. In other embodiments, each bundle 20 may be held with the fibers together (untwisted) and twisted only once to the other bundles to form the construct 30. The bundle arrangement shown in FIG. 2B forms a thirty fiber construct 30. FIG. 2D also illustrates that the twisted construct 30 can include a first end portion that is tied into a knot 30*k* and another end portion that has a biocompatible absorbable or other biocompatible coating forming an aglet 30*e*. Other twist-retention end portion configurations can be used, including both end portions tied into knots 30*k* or both ends having the aglet 30*e* other untwist members such as ties, staples, and the like may be used. Thus, one or both end portions of the construct 30 may be secured with a closure material and/or device 35 such as a clamp, tie, staple or other holder, including tape or may be secured using heat and/or a coating 30*e* or adhesive and the like, or a knot 30*k*, such as a simple loop knot to secure the twist configuration.

The two-strand arrangement of FIGS. 1A and 1B may be particularly suitable for a two-holder twisting device that rotates to place the twists while the three group arrangements of FIGS. 2A-2C may be suitable for a three-strand turning device. Other devices may be able to twist greater numbers of strands and the instant invention is not limited to the use of two or three strands or bundles.

Figure 3A:
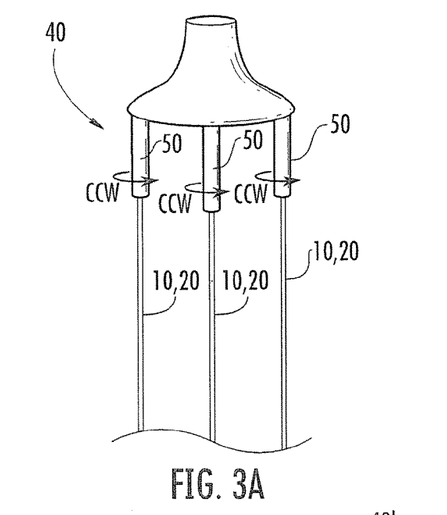
FIGS. 3A and 3B are schematic illustrations of a three-strand twisting apparatus that can serially and substantially continuously turn the strands in a clockwise and/or counter-clockwise direction to form a twisted length of medical construct according to embodiments of the present invention.
Figure 3B:
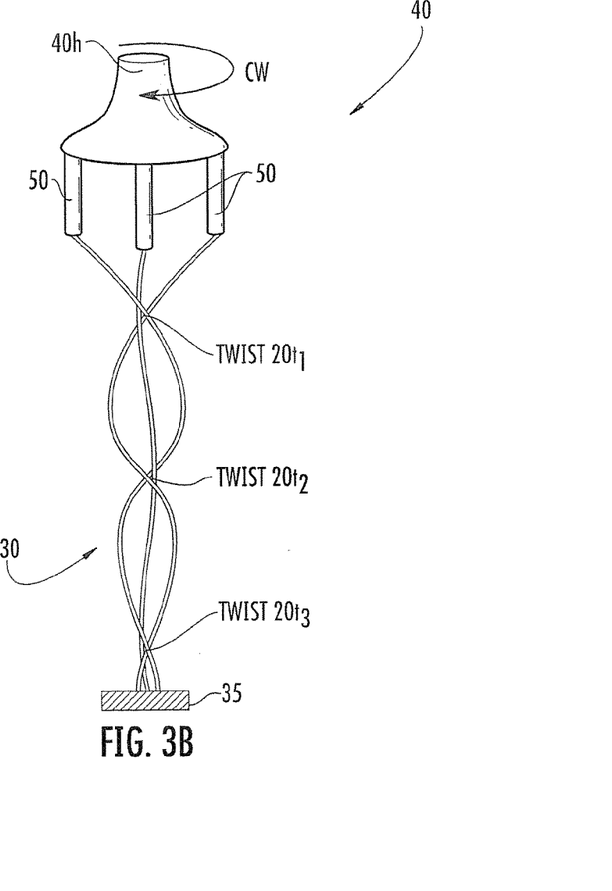

FIGS. 3A and 3B are schematic illustrations of a three post rotating head 40 turning device that may be used to hold an end portion of the fibers/bundles 10, 20 and turned in a counterclockwise (CCW) or clockwise (CW) direction to form the twists in the fibers 10 and/or bundles 20. As shown in FIG. 3A, three strands of fibers (single or multiple) are attached to the three posts 50 and the other end of the fibers/bundles are held in tension, such as against an assembly board or anchor. The posts 50 of the device 40 are simultaneously individually rotated in the CCW direction and start forming twists on each fiber 10 (or fiber bundle 20) from the end away from the device up to the head of the device 40*h*. After the twists are formed into the fibers 10/bundles 20, the head 40*h* can be rotated as shown in FIG. 3B. As shown, the device 40 can be rotated in the opposing direction (shown as CW) typically for at least about 50% of the number of turns used to form the twists in the individual fibers 10 or fiber bundles 20 to inhibit the construct from uncurling or untwisting. The reverse turning can be for between about 50% to about 300% (e.g., in some embodiments about substantially the same) of the number of turns as the original direction and may be carried out under tension. As discussed above, the end portions of the construct 30 may be secured with a closure material and/or device 35 such as a clamp, tie, staple or other holder, including tape, heat, coating 30e or adhesive and the like, and/or a knot 30k, such as a simple loop knot, may be tied in the construct to secure the twist configuration.

It is contemplated that devices corresponding to hair styling "2-3 strand" devices may be useful to carry out the turning of fibers in smaller lot size or production environments. These devices are semi-automated (battery operated) and, once the fibers or bundles of fibers are mounted to the rotating head, can be rotated to turn the fibers to form the twists in the desired density (twists per fiber centimeter). See, e.g., QUICK BRAID STYLING KIT from Conair, Inc. and IGIA AT6746S Twist-A-Braid Hair Braider for two and three strand twists from IGIA. See also, U.S. Patent Application Publication 2003/0230316, the contents of which are hereby incorporated by reference as if recited in full herein. It is also contemplated that textile or conventional twine or rope equipment can be modified to provide a mass-production scale system to form the medical twisted cables. Automated spinning and twisting equipment in the textile and twine/rope industries are also well known. For an overview of the rope making process and cotton-spinning machines, see, e.g., url 1911encyclopedia.org/Rope And Rope-Making, and url 1911encyclopedia.org/Cotton-spinning-machinery (both from the Classic Encyclopedia based on the 11th edition of the Encyclopedia Britannica (pub. 1911).

The twisted constructs 30 can be formed into substantially tubular construct, or other suitable configuration. Some constructs may be particularly suitable for a ligament prosthesis, such as for an ACL repair or replacement. Other constructs 30 may be particularly suitable as a tendon-prosthesis, such as, for example, the flexor tendon. The construct 30 can be sutured, tied, knotted, stapled, anchored or otherwise mounted directly to a cut tendon or ligament or may be attached to bone (including bone anchors, bone tunnels and/or bone suture anchors). A construct forming a suture 30s may be particularly suitable for AC joint repairs. In some embodiments, a twisted suture 30s can be used to attach the twisted cable (e.g., rope 30c, 30r) to the target repair site. In some embodiments, a plurality of the cables 30, can be used to treat a target site. For example, one or more of the larger size cables (e.g., ropes 30r) can be used with one or more sutures 30s to treat the target site (e.g., between about 5-32 suture sized cables and/or between about 2-4 larger sized cables). Other twist configurations may also be used as suitable for the target treatment site/prosthesis. For some Achilles tendon repairs, a twisted construct 30 of between about 2000-4000 fibers may be used.

It is contemplated that the twisted suture, rope or cable construct (or combinations of same) may be particularly suitable for treating AC joint separation of the shoulder. The construct 30 may also be suitable for a Hallus valgus correction, for a tarsometatarsal injury repair and syndesmotic trauma repair. Holes can be drilled in the local bone structure, e.g., chromium process and clavicle and the cable construct 30 can be inserted/attached to treat the AC separation.

As desired, the body of the construct 30 can include a smooth outer sheath that may be formed by a coating, gel or other material. In particular embodiments, the construct 30 can comprise polyglycolic acid, polylactic acid, or combinations of these or other substances.

The twist pattern can be a relatively tight twist or a relatively loose twist, the latter typically with less structural rigidity and more conformability than a tight twist. However, the desired number of fibers used and the configuration/twist density can depend on the target location and the desired mechanical properties and configuration of the repair. Exemplary twist densities can be between about 10-300 turns per fiber meter, including about 1 turn per 10 cm of fiber or strand to about 1 turn per mm of fiber or strand, typically between about 1-2 turns per fiber-cm, including, for example, about 110 turns per fiber meter.

The twisted construct 30 can be configured to elastically stretch between about 10-30% when under a normal load for an anatomic use, such as, for example a ligament repair, such as an AC and/or ACL repair.

The twisted construct 30 can provide immediate mechanical stability and be biodegradable over time to act as a relatively temporary or acute scaffold for body repairs. In some embodiments, the twisted construct 30 can have a half life of about 20-60 weeks, but mechanical properties may degrade more rapidly, but the construct 30 typically provides sufficient mechanical fixation when exposed to normal body conditions in vivo for a repair of at least about 1 week, typically about 1 month to at about 3 months and also provides a scaffold to promote tissue in-growth.

In some embodiments, the construct 30 is between about 0.5-50 cm long, typically between about 1-25 cm. In some embodiments, the construct 30 is between about 2 cm to about 20 cm long, and in some embodiments about 15 cm long. As discussed above, the construct 30 may have a diameter that is typically between about 1 mm to about 5 mm (dry, on average), but larger or smaller sizes may be used. In particular embodiments, the construct 30 can be a homogenous twisted cable with the fibers therein being only (NDGA treated) collagen fibers. In some embodiments, the cable 30 can have between about 90-270 NDGA treated collagen fibers and the strands or groups of fibers can be twisted together with between about 200-300 twists per meter on average.

Figure 4:
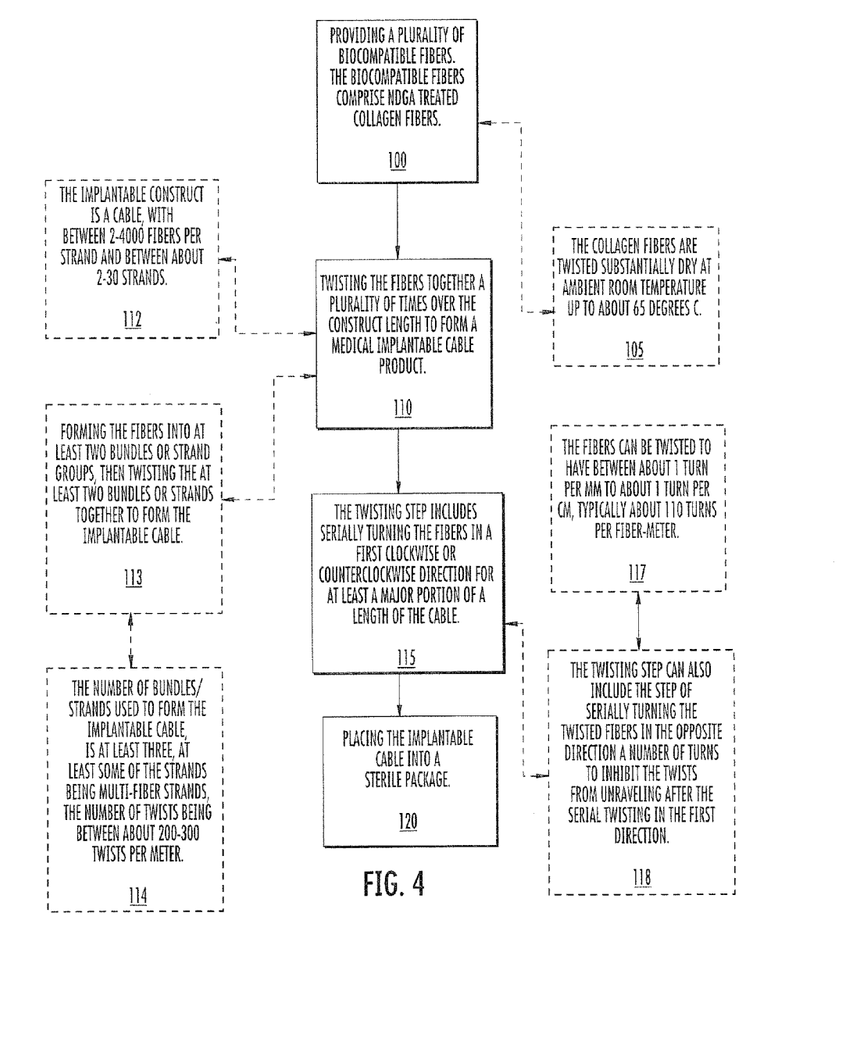
FIG. 4 is a flow chart of operations that can be used to carry out embodiments of the invention.

FIG. 4 illustrates operations that may be carried out to produce constructs 30 according to embodiments of the invention. A plurality of biocompatible NDGA treated collagen fibers are provided (block 100). The fibers are twisted a plurality of times over their length (block 110). The twisting step includes serially turning the separate fibers or separate strands of fibers (see, e.g., FIG. 3A) either CW or CCW a plurality of times for at least a major portion of a length of the construct (block 115). The twisting can done for each fiber or groups of fibers serially or substantially simultaneously (FIG. 3A illustrates a simultaneous process).

The separate fibers or groups of fibers can be twisted in a CW or CCW direction to have a suitable number of turns/twists per fiber meter, such as, for example, between about 2-300, including between about 1 turn per mm to about 1 turn per cm fiber, such as, for example, about 110 turns per fiber meter (block 117). The twisting can be carried out so that three or more fibers or fiber bundles are twisted simultaneously (see, e.g., FIG. 3A).

A second twisting step can then twist (e.g., turn) the previously twisted fibers together in the opposite CW or CCW direction at least about 50% of the number of original turns made in the first direction after the serially turning in the first direction (block 118) (see, e.g., FIG. 3B) to interlock the twists in a multi-directional twist configuration of twisted fiber bundles to form a cable (e.g., rope or suture, depending on size). The reverse turning of the original twisted fibers can be carried out to twist the twisted fibers/fiber bundles with between 50%-300% of the number of turns or twists made in the separate fibers or fiber groups, and may be carried out with substantially the same twist density) and while under tension to cause an interlocking of the twisted fibers and inhibit the original twist direction from unraveling. For example, the separate fibers or groups of fibers can have about 100 twists per fiber meter, on average, and those twisted fibers or groups of fibers can be twisted together with about 200-300 twists per meter, on average. The implantable construct (e.g., cable) can be placed in a sterile package (block 120).

The collagen fibers can be twisted substantially dry at ambient room temperature up to about 65 degrees Celsius (block 105). The fibers can be arranged into bundles/strands of substantially parallel fibers before the twisting step.

The construct can have between about 2-4000 fibers per strand/bundle and/or between about 30-360 strands/bundles (block 112). The fibers can be formed into at least two bundles/strands, then the twisting can be twisting the at least two bundles/strands together to form the construct (113). The number of bundles/strands can be at least three (block 114).

In some embodiments, the construct can be used for a ligament repair or replacement. In other embodiments, the construct can be used for a tendon repair or replacement. The medical construct 30 can have a tensile strength, stiffness and dynamic (elastic stretch) flexibility that meet or exceeds that of a pre-injury natural ligament and/or tendon undergoing treatment. Optionally, the twisted construct can be implanted in a patient using one or more of a suture, suture anchor, bone anchor, bone tunnel, staple and the like.

Also, the construct 30 can optionally include, e.g., be coated, impregnated and/or amalgamated with, a gel or other material. The coating may be to promote fibroblasts, and/or comprise one or more of an anti-inflammatory agent, an antibiotic or other therapeutic agent.

The twisted construct 30 is biocompatible and may be biodegradeable (e.g., absorbed over time).

In some embodiments, the constructs 30 can be configured to have greater tensile strength, stiffness and dynamic flexibility as corresponding natural tissue, e.g., natural ligament or tendon fibers.

In some embodiments, the collagen fibers that are used to form the twisted construct or cable can consist essentially of collagen fibers formed in any suitable manner to be acceptable as a biomedical implant/construct.

As noted above, in particular embodiments, the fibers can comprise NDGA-treated collagen. Suitable ways of forming NDGA-polymerized and/or -treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products. However, as noted below, other collagen fiber production processes may be used to produce sufficiently high-strength elongate collagen fibers.

As has been established by the inventors, NDGA-treated collagen fibers are biocompatible and have desirable mechanical properties. For additional discussion of the NDGA polymerized fibers, see, Thomas J. Koob, *Biometic approaches to Tendon Repair*, Comparative Biochemistry and Physiology Part A 133 (2002) 1171-1192.

In some embodiments, the (NDGA) collagen fibers may be high-strength. The term "high-strength" refers to fibers having an average tensile strength of at least about 150 MPa, such as between about 180 MPa and 350 MPa, and typically between about 180 MPa and 280 MPa, such as between about 240-279 MPa (measured on average). The fibers may also have suitable stiffness and strain yield for target treatments. In general, the fibers can have a stiffness of at least about 200 MPa (e.g., at least about 300, 400, 500, or 600 MPa), and a strain at failure of less than about 20% (e.g., less than about 15 or 10%). The fibers may be formed with a relatively thin diameter, such as, for example about a 0.07 mm dry diameter (on average) and about a 0.09 mm wet diameter (on average).

In some embodiments, collagen fibers can be manufactured using preparatory donor collagen material that may be can be pepsin-derived or solubilized collagen that is processed/purified. In this embodiment, the purified collagen preparatory material is dialyzed a plurality of times in a selected liquid for a desired period of time. The dialyzing is typically repeated three times. The dialyzing can be carried out against dionized (DI) water in a volume ratio of between about 30:1 to about 100:1, typically about 60:1, for between about 30-90 minutes, typically about 40 minutes. The dialyzing can form a substantially clear gel of collagen fibrils indicating good organization (substantially parallel fibrils), where opacity indicates less organization. The organization can help improve tensile strength of subsequently cross-linked fibers.

The dialyzed collagen material can be incubated for a desired time before placing in a fiber-forming buffer. The dialyzed gel can be cross-linked to provide collagen fibers for medical constructs. The polymerization (e.g., cross-linking) can be carried out using NDGA and the resultant NDGA-treated collagen fibers can be relatively thin, such as, for example, about 0.08 mm dry diameter (on average).

The incubation may be for at least about 24 hours, typically 24-48 hours, and may be at room temperature of between about 15-30° C., typically about 25° C. The dialysis process can be used before cross-linking for subsequent use with any suitable cross-linking materials, such as, for example, to promote collagen organization, and the process is not limited to NDGA, but may be useful with other materials, including, for example, glutaraldehyde. For additional discussion of methods used to form high-strength NDGA treated collagen fibers, see, U.S. patent application Ser. No. 11/964,756, the contents of which are hereby incorporated by reference as if recited in full herein. Other methods to make the collagen fibers of sufficiently high strength and diameter suitable for their intended biomedical uses may also be used and the present invention is not limited to any particular collagen fiber production process.

Figure 5A:
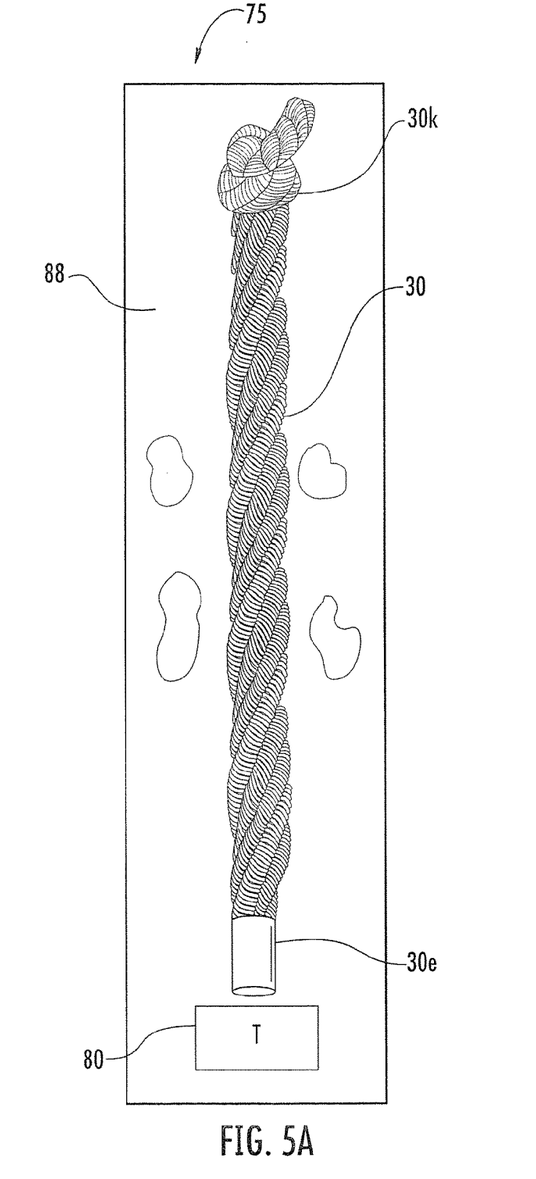
FIGS. 5A-5C are schematic illustrations of exemplary medical kits according to embodiments of the invention.
Figure 5B:
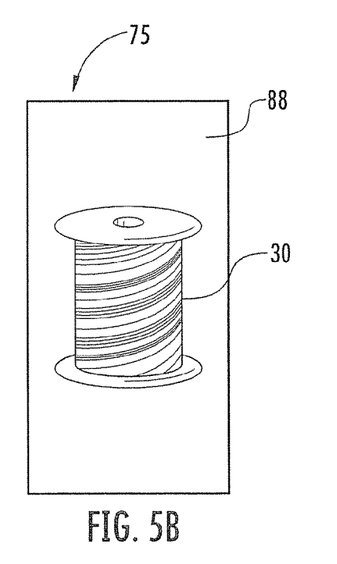
Figure 5C:
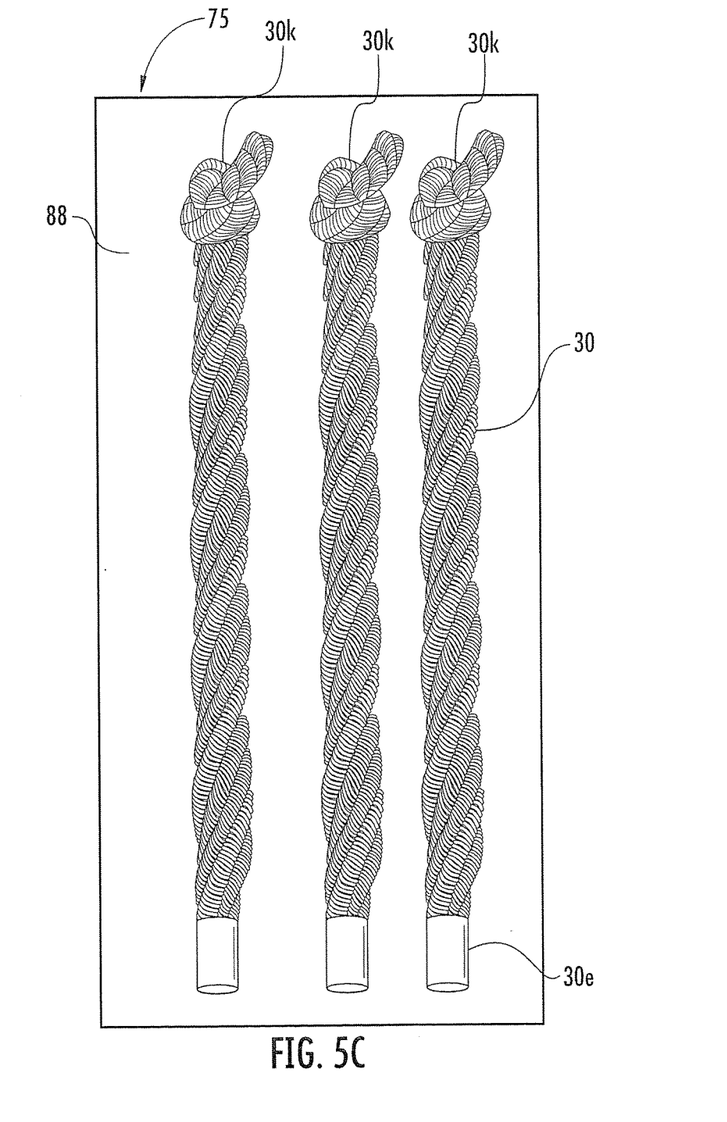

FIG. 5A illustrates a medical kit 75 that includes at least one construct 30. As shown, the construct 30 can have one or more end portions encased in a flexible biocompatible coating, such as a cyanoacrylate bond material and/or adhesive. Alternatively, or additionally, as shown in FIG. 5C, one or both ends of a construct 30 may be tied into a knot 30k. If the construct is a suture 30s, it may be provided as a bone anchor or an atraumatic or traumatic needle with suture. The kit 75 may include other components, such as, for example, a container of surgical adhesive, an anchor, staple, and the like. The construct 30 may be held hydrated in a flexible sealed package of sterile liquid 88. The kit 75 may include a temperature warning so that the construct 30 is not exposed to unduly hot temperatures that may degrade the implant. A temperature sensor 80 may optionally be included on or in the package 88 of the kit 75 to provide a visual or audible alert to a clinician as to any excessive or undue temperature exposure prior to implantation. FIG. 5B illustrates that the twisted construct 30 may be provided on a solid substrate such as a spool 90 in a package 88. FIG. 5C illustrates that the kit 75 can include a plurality of the twisted constructs 30.

Particular exemplary uses of the construct 30 are briefly described below.

Use 1

Repair of AC joint separation of the shoulder. The AC joint is between the clavicle (collarbone) and acromion (shoulder blade). The construct 30 can be used to repair the AC joint separation. The construct 30 can be used to replace and/or repair AC ligaments that surround and support the AC joint. The construct 30 may also be used to repair one or both of the two other ligaments, the coracoclavicular ligaments, that hold the clavicle down by attaching it to a bony knob on the scapula called the coracoid process. The construct 30 can comprise between about 90-270 collagen fibers in a suitable length that is typically between about 10-15 cm. The collagen fibers can be configured into groups or bundles of fibers that are first twisted individually in one direction, then the twisted bundles of fibers are twisted together in another direction. One or both ends of the twisted fiber construct 30 can include a flexible biocompatible coating 30e as noted above that helps keep the twisted construct from unraveling. The construct 30 can have a twist density of between about 200-300 twists per meter (twisted fiber length), on average.

Use 2

Hallus valgus/Hallax valgus correction. The construct 30 can be used to stabilize bones in conjunction with a Hallus valgus procedure. The construct 30 can comprise between about 3-270 collagen fibers in a suitable length that is typically between about 2-15 cm. The collagen fibers can be configured into a single fiber or groups or bundles of fibers that are first twisted individually in one direction, then the twisted fibers or bundles of fibers can be twisted together in another direction. One or both ends of the twisted fiber construct 30 can optionally include a flexible biocompatible coating 30e as noted above that helps keep the twisted construct from unraveling.

Use3

UCL repair. The "ulnar collateral ligament" repair is also kcnown as a "Tommy John" surgery. The construct 30 can be used to replace a ligament in the medial elbow (rather than a tendon from elsewhere in the body, often from the forearm, hamstring, knew or foot of the patient). The procedure is common among collegiate and professional players in several sports, most notably baseball. The construct 30 can be inserted (potentially in a figure-8 formation although not required) through tunnels that have been drilled in the ulna and humerus bone that are part of the elbow joint.

The construct 30 can comprise between about 90-270 collagen fibers in a suitable length that is typically between about 10-15 cm. The collagen fibers can be configured into groups or bundles of fibers that are first twisted individually in one direction, then the twisted bundles of fibers are twisted together in another direction. One or both ends of the twisted fiber construct 30 can include a flexible biocompatible coating 30e as noted above that helps keep the twisted construct from unraveling. The construct 30 may be configured with the twisted fibers/bundles of fibers twisted together with between about 200-300 twists per meter.

Use 4

ACL repair. The construct 30 can be used as a replacement or for repair of an anterior cruciate ligament (ACL). The construct 30 can be used to attach the ends of bones together or attached to one end of a torn natural ligament and the other end to bone. The construct 30 can replace or supplement an ACL at the center of the knee joint where the construct 30 can run from the backside of the femur (thighbone) to connect to the front of the tibia (shinbone).

The construct 30 can comprise between about 90-270 collagen fibers in a suitable length that is typically between about 10-15 cm. The collagen fibers can be configured into groups or bundles of fibers that are first twisted individually in one direction, then the twisted bundles of fibers are twisted together in another direction. One or both ends of the twisted fiber construct 30 can include a flexible biocompatible coating 30e as noted above that helps keep the twisted construct from unraveling. The construct 30 may be configured with the twisted fibers/bundles of fibers twisted together with between about 200-300 twists per meter.

Use 5

Spinal cables/wires. The constructs 30 can be used for stabilizing the spinal column such as by connecting vertebrae for spinal stabilization, including, for example, interspinous reinforcement or posterior spinal fixation. The constructs 30 can be used for fixation or stabilization of cervical, thoracic and/or lumbar fractures. Currently stainless steel wires are used with respect to a Rogers' technique, a Bohlman technique and/or facet wiring. The constructs 30 can be used in lieu of or with the conventional wires or cables for any of these and similar procedures.

The spinal constructs 30 can comprise between about 30-270 collagen fibers in a suitable length that is typically between about 3-15 cm. The collagen fibers can be configured into groups or bundles of fibers that are first twisted individually in one direction, then the twisted bundles of fibers are twisted together in another direction. One or both ends of the twisted fiber construct 30 can include a flexible biocompatible coating 30e as noted above that helps keep the twisted construct from unraveling. The construct 30 may be configured with the twisted fibers/bundles of fibers twisted together with between about 200-300 twists per meter.

Use 6

Figure 2E:
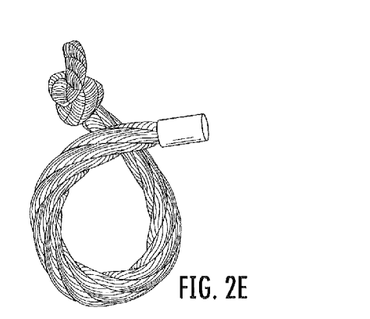
FIG. 2E is a schematic illustration of a twisted construct in a loop configuration according to embodiments of the present invention.

Cerclage treatments. The construct 30 can be used for cerclage uses such as for repair of oblique bone fractures or soft tissue repair. The construct may also be used for reinforcing a cervix for a cervix-cerclage treatment (instead of suturing the cervix closed or for reinforcement), which is typically used during pregnancy. The construct 30 can be formed in situ or preformed as an encircling twisted collagen fiber loop or ring (see, e.g., FIG. 2E). In some embodiments, the construct 30 is a bone cerclage that brings together the ends of an obliquely fractured bone or the fragments of any target bone fractures, such as, for example, a broken patella, metacarpal or proximal phalanx of the fingers.

The construct 30 can comprise between about 90-270 collagen fibers in a suitable length that is typically between about 10-15 cm. The collagen fibers can be configured into groups or bundles of fibers that are first twisted individually in one direction, then the twisted bundles of fibers are twisted together in another direction. One or both ends of the twisted fiber construct 30 can include a flexible biocompatible coating 30e as noted above that helps keep the twisted construct from unraveling. The construct 30 may be configured with the twisted fibers/bundles of fibers twisted together with between about 200-300 twists per meter.

The present invention is explained in greater detail in the following non-limiting Examples.

EXAMPLES

Figure 6:
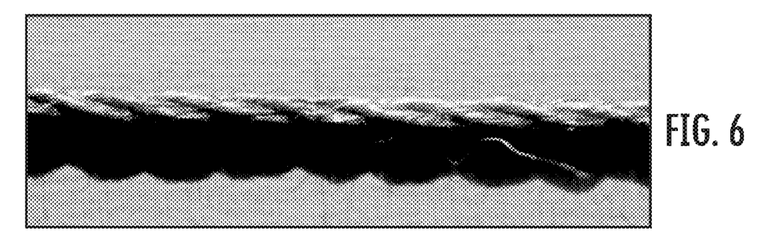
FIGS. 6-8 are digital images of three different twisted cable configurations according to embodiments of the invention.
Figure 7:
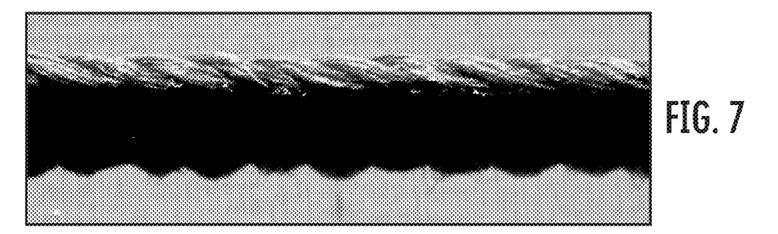
Figure 8:
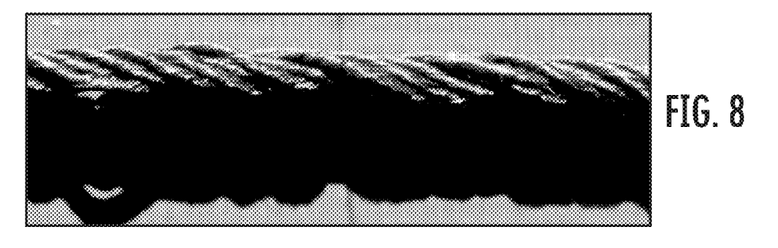

FIGS. 6, 7 and 8 illustrate exemplary twisted cables of NDGA-collagen fibers. The average size of the fibers 10 was about 80 microns (dry). The fibers were twisted dry and at room temperature. The starting fibers had a length of between about 1 m to about 1.5 m. (it is contemplated that longer fibers can be obtained in the future). The number of turns or twists formed in the fibers was about 110 turns per fiber meter on average. The twisting was carried out by using the three-strand holder CONAIR QUICK BRAID STYLING KIT. Subsequent prototypes were made by hand twisting with each fiber held substantially under equal tension. It is envisioned that a motorized twisting device can be developed for spooled fibers.

FIG. 6 is a photograph of a 30 fiber collagen cable, 10×3: 10 twisted fibers/strand ×3 strands twisted together.

FIG. 7 is a photograph of a 108 fiber cable, 4×3×3×3: 4 twisted fibers/strand ×3 strands twisted together ×3 of the former twisted together ×3 of the former twisted together.

FIG. 8 is a photograph of a 180 fiber cable, 20×3×3: 20 fibers twisted/strand ×3 strands, then three (60 fiber) twisted strands (3×60) twisted together.

Figure 9:
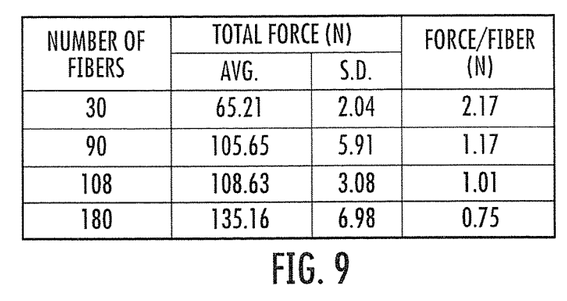
FIG. 9 is a table of tensile strength shown in total Force (N) versus Force/fiber (N) for four different twisted NDGA treated collagen cable configurations according to embodiments of the present invention.
Figure 10:
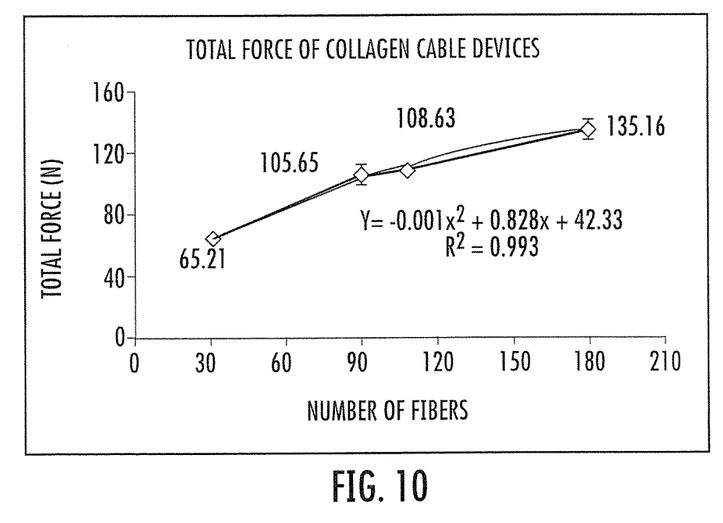
FIG. 10 is a graph of tensile strength in total Force (N) versus number of fibers corresponding to the data shown in FIG. 9.

FIG. 9 is a table summarizing the tensile strength in total force (N) and Force/Fiber (N) for four different (wet) cable configurations (with different numbers of fibers). It is believed that the declining tensile strength as the cables increase in fiber number is attributed to the variation in the forming process. Also, the number of twists and twist configurations are likely to affect the mechanical properties. FIG. 10 is a graph of tensile strength shown as total Force (N) versus number of fibers for the data shown in FIG. 9.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A medical construct, comprising:
three biocompatible cables twisted together,
wherein each biocompatible cable comprises three strands twisted together about 200-300 twists per fiber meter in a first rotative direction, and
wherein each strand comprises twenty NDGA-treated elongate collagen fibers twisted together a number of twists per fiber meter in a second rotative direction opposite the first rotative direction.

2. A medical construct, comprising:
at least one biocompatible cable comprising a plurality of strands twisted together a number of twists per fiber meter in a first rotative direction,
wherein each strand comprises a plurality of NDGA-treated elongate collagen fibers twisted together a number of twists per fiber meter in a second rotative direction opposite the first rotative direction, said number of twists per fiber meter in the second rotative direction being substantially the same in each of the strands, and
wherein said construct comprises between about 2000-4000 NDGA-treated elongate collagen fibers.

* * * * *

UNITED STATES PATENT AND TRADEMARK OFFICE
CERTIFICATE OF CORRECTION

PATENT NO.        : 9,216,077 B2  
APPLICATION NO.   : 12/465433  
DATED             : December 22, 2015  
INVENTOR(S)       : Davis et al.

Page 1 of 1

It is certified that error appears in the above-identified patent and that said Letters Patent is hereby corrected as shown below:

In the Specification:

Column 5, Line 12: Please correct "50μm" to read -- 50nm --

Column 5, Line 58: Please correct "Vicryl(V Polymer,"
                    to read -- Vicryl® Polymer, --

Column 6, Line 50: Please correct "between 0.0 mm"
                    to read -- between 0.01 mm --

Signed and Sealed this  
Seventh Day of June, 2016

Michelle K. Lee  
*Director of the United States Patent and Trademark Office*